United States Patent [19]
Jarrett et al.

[11] Patent Number: 4,791,929
[45] Date of Patent: Dec. 20, 1988

[54] BIOABSORBABLE COATING FOR A SURGICAL ARTICLE

[75] Inventors: Peter K. Jarrett, Trumbull; Donald J. Casey, Ridgefield; Leonard T. Lehmann, Danbury, all of Conn.

[73] Assignee: American Cyanamid Company, Stamford, Conn.

[21] Appl. No.: 172,601

[22] Filed: Mar. 24, 1988

Related U.S. Application Data

[63] Continuation-in-part of Ser. No. 910,598, Sep. 23, 1986, abandoned.

[51] Int. Cl.$^4$ .............................................. A61L 17/00
[52] U.S. Cl. ................................. 128/335.5; 528/354; 528/361; 428/395
[58] Field of Search ....................... 528/354, 359, 361; 428/395; 128/335.5

[56] References Cited

U.S. PATENT DOCUMENTS

| | | | |
|---|---|---|---|
| 3,982,543 | 9/1976 | Schmitt et al. | 427/2 X |
| 4,027,676 | 6/1977 | Mattei | 427/2 X |
| 4,048,256 | 9/1977 | Casey et al. | 525/444 |
| 4,057,537 | 11/1977 | Sinclair | 528/354 |
| 4,201,216 | 5/1980 | Mattei | 128/335.5 |
| 4,595,713 | 6/1986 | St. John | 528/354 X |
| 4,605,730 | 8/1986 | Shalaby et al. | 528/354 X |
| 4,624,256 | 11/1986 | Messier et al. | 128/335.5 |

*Primary Examiner*—Earl Nielsen
*Attorney, Agent, or Firm*—Charles F. Costello, Jr.

[57] ABSTRACT

A bioabsorbable coating for a surgical article comprises a copolymer manufactured from the monomer caprolactone and at least one other copolymerizable monomer. The surgical article can be a bioabsorbable suture or ligature.

26 Claims, No Drawings

BIOABSORBABLE COATING FOR A SURGICAL ARTICLE

CROSS-REFERENCE TO RELATED APPLICATION

This is a continuation-in-part application of U.S. Ser. No. 06/910,598 filed Sept. 23, 1986, now abandoned.

BACKGROUND AND SUMMARY OF THE INVENTION

A bioabsorbable coating for a surgical article comprises a copolymer manufactured from the monomer caprolactone and at least one other copolymerizable monomer. The surgical article can be a bioabsorbable suture or a ligature. The surgical suture or ligature coated with the bioabsorbable copolymer has improved knot repositioning properties.

The bioabsorbable coating of this invention has advantages over prior art coatings used with surgical sutures or ligatures. Specifically, sutures coated with the copolymer coating of this invention are less stiff than sutures using the coating described in the prior art; see examples 6 and 10 in U.S. Pat. Nos. 3,867,190 and 3,736,646 which are incorporated herein by reference. Also, the processes for coating a bioabsorbable surgical article are not clearly described in the prior art. That is, the process of this invention uses a copolymer manufactured from at least about 50 percent by weight of the monomer caprolactone and the remainder glycolide. Copolymers of these proportions are soluble in acetone, as contrasted with, for example, the copolymers of lactide and glycolide discussed in U.S. Pat. No. 4,201,216, which is incorporated herein by reference.

The use of a copolymer of caprolactone and glycolide as a suture is known in the prior art, for example, as disclosed in U.S. Pat. Nos. 4,700,704 (e.g. claim 1) and 4,605,730 (examples I to XI), and in example 5 of U.S. Pat. Nos. 4,300,565 and 4,243,775. All of these patents are incorporated herein by reference.

The use of a copolymer of at least 90% by weight caprolactone and another biodegradable monomer, e.g. glycolide, as a coating is disclosed in U.S. Pat. No. 4,624,256. See also U.S. Pat. Nos. 4,190,720 (column 1) and 3,942,532 (example II), which are disclosed in the U.S. Pat. No. 4,624,256. These two latter patent disclose a copolymer U.S. Pat. No. 4,190,720 or homopolymer U.S. Pat. No. 3,942,532 of e-caprolactone. In the U.S. Pat. No. 4,190,720, the copolymer is disclosed as a film; in the U.S. Pat. No. 3,942,532 the homopolymer is disclosed as a suture coating. It is not seen in either of the latter two patents where the respective polymers are disclosed as bioabsorbable. All of these patents are incorporated herein by reference.

The bioabsorbable coating of this invention has superior and unexpected results over the known commercially available surgical suture or ligature coatings. For example, the coating of this invention does not present a hazy appearance on a suture. The coating can be dissolved in acetone which seems to be less deleterious than other known solvents, for example, methylene chloride. Further, suture characteristics such as knot-snug-in or repositioning, knot security, and tissue drag appear to be equal to, if not better than suture coatings disclosed in the prior art.

The copolymers described in this invention are random. The term random copolymer means the result of a copolymerization reaction in which all of the monomers are charged into the reactor simultaneously. It is to be understood that variations in reaction conditions can lead to some differences in the actual degree of randomness with respect to the distribution of comonomer units in a copolymer chain.

A bioabsorbable coating for a surgical article has been invented. The coating comprises a random copolymer, from about 50 to 85 percent by weight of the copolymer consisting of linkages of formula (I):

and the remaining linkages comprising at least one of the formulas (II) to (VIII):

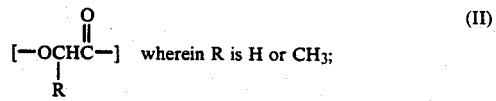

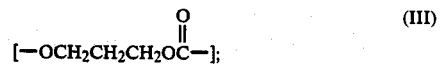

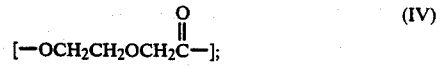

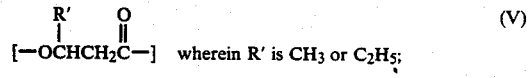

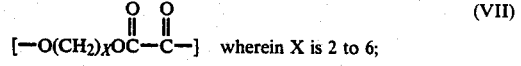

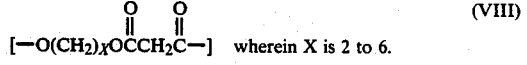

In one embodiment, the remaining linkages are selected from the group consisting of formulas (II) and (III). In another embodiment the remaining linkages are selected from the group consisting of formula (II).

In a specific embodiment, the formula (II) is:

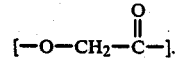

In another specific embodiment, the formula (II) is:

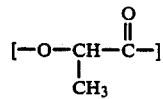

In still another embodiment, formula (I) is from about 65 to 85 percent by weight. In a further embodiment, the inherent viscosity of the copolymer is about 0.2 to 1.4 dl/g (0.5 g/dl in CHCl$_3$, 30° C.) and the melting point is less than about 50° C.

It is to be understood that the term strand as used in this invention can be either a multifilament or a monofilament. A multifilament is preferred. The multifilament strand can be a braid.

The surgical article coated with the above described polymers can be bioabsorbable. In one embodiment, the bioabsorbable surgical article is a suture or ligature. In a specific embodiment, the suture or ligature is manufactured from a polymer prepared from one or more monomers selected from the group consisting of lactides, carbonates and lactones. If the polymer in a strand, for example a suture or ligature, and the copolymer in the coating are prepared from the same monomers, it is to be understood that the copolymer in the coating has a melting point of less than about 50° C. or is noncrystalline, that is amorphous. It is to be further understood that this description applies by implication to the description of the invention in the claims.

In a more specific embodiment, the suture or ligature is manufactured from a homopolymer prepared from the monomer glycolide. In another more specific embodiment, the suture or ligature is manufacture from a homopolymer prepared from the monomer lactide. In yet another more specific embodiment, the suture or ligature is manufactured from a copolymer prepared from the monomers glycolide and 1,3-dioxan-2-one. In a further specific embodiment, the suture or ligature is manufactured from a copolymer prepared from the monomers glycolide and lactide.

The suture or ligature can be in multifilamentary form. In a specific embodiment, the coating comprises about 1/10 to 5% by weight of the coated multifilamentary suture or ligature. In a more specific embodiment, the coating comprises about ½ to 3% by weight of the coated multifilamentary suture or ligature. In the more specific embodiment, the coating can comprise up to about 1½ percent by weight of the coated multifilamentary suture or ligature.

A process for coating a bioabsorbable surgical article has also been invented. The process comprises dissolving in acetone a random copolymer, from about 65 to 85 percent by weight of the copolymer consists of linkages of formula (I):

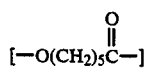

and the remaining linkages comprise at least one of the formulas (II) and (III):

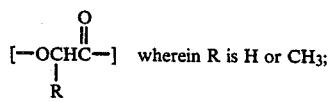 wherein R is H or CH₃;

contacting the surgical article with the dissolved copolymer; maintaining the contact between the surgical article and dissolved copolymer until the copolymer on the surgical article comprises from about 1/10 to 5% by weight of the coated surgical article; removing the coated surgical article from the dissolved copolymer; and drying the copolymer coating on the surgical article. Parameters to be used in the maintaining step are more fully described, e.g., in U.S. Pat. Nos. 4,716,203, 4,711,241 and 4,047,533, all of which are incorporated herein by reference. It is to be understood that the amount of pickup described in these patents can be increased or decreased by any person skilled in the art without undue experimentation. As a general statement, only one pass is required to obtain a coating comprising less than about 2 percent by weight of the coated strand. For a coating comprising more than about 2 percent to about 4 percent by weight of the coated strand, two passes are generally found to give a more uniform coating level. For coating levels from 4 to 5 percent, three passes will probably give the most uniform coating level.

In one embodiment, the caprolactone is $\epsilon$-caprolactone.

DESCRIPTION OF THE PREFERRED EMBODIMENT(S)

The following examples describe the best mode of making the using the copolymers of this invention. Unless otherwise specified, all of the inherent viscosity ($\eta$inh) measurements in the examples were conducted at 30° C. Inherent viscosities are expressed in units of deciliters per gram (dl/g). The solution concentrations used to measure $\eta$inh are expressed in units of grams of polymer per deciliter of solution and are set in parentheses following the $\eta$inh value. The solvents used were either chloroform ($CHCl_3$) or hexafluoroacetone sesquihydrate (HFAS).

A description of inherent viscosity using the nomenclature described above is disclosed in the prior art, e.g. in Kinematic Glass Viscometers, ASTM D 2515; Dilute Solution Viscosities of Polymers, ASTM D 2857; Dilute Solutio Viscosity of Ethylene Polymers, ASTM D 1601; Techniques of Polymer Characterization; P. Allen, Ed. Butterworth Scientific Publications, London 1959, chapter 6; Kirk-Othmer Encyclopedia of Chemical Technology, Second Ed., John Wiley & Sons, 1968 vol 16 pages 242–253; and Polymer Handbook, J. Brandrup & E. Immergut, Ed., Interscience, NY pages IV-1 to IV-2. All of this prior art is incorporated herein by reference.

EXAMPLE 1

$\epsilon$-Caprolactone Homopolymer

A sample of $\epsilon$-caprolactone homopolymer was purchased from Scientific Polymer Products, Inc. The sample $\eta$inh was measured as 0.27 dl/g (0.5 g/dl in $CHCl_3$). GPC analysis in $CH_2Cl_2$ using polystyrene standards gave MW=17,600 and MN=8500.

EXAMPLE 2

Synthesis of $\epsilon$-Caprolactone Homopolymer $\epsilon$-Caprolactone (10 g, 0.088 mole), lauryl alcohol (0.122 g, $6.57 \times 10^{-4}$ mole) and stannous chloride dihydrate (0.988 mg, $4.38 \times 10^{-6}$ mole) were combined in a flask. The flask was flushed with nitrogen and evacuated. The flask was heated at 135° C. in an oil bath for 24 hours. The resulting polymer had an $\eta$inh of 0.53 dl/g (0.5 g/dl in HFAS). GPC analysis in $CH_2Cl_2$ using polystyrene standards gave MW=65,200 and MN=26,900.

EXAMPLE 3

Synthesis of $\epsilon$-Caprolactone-1-Lactide Copolymer $\epsilon$-Caprolactone (212.5 g, 1.86 mole), 1-lactide (37.5 g, 0.26 mole), lauryl alcohol (4.10 ml, 0.018 mole) and stannous chloride dihydrate (35.9 mg, $1.59 \times 10^{-4}$ mole) were combined in a stirred reactor under nitrogen at 175° C. The mixture was stirred at 175° C. for 3 nitrogen. The resulting polymer had a composition, as determined by $^1$H NMR, of 84 wt. % ε-caprolactone and 16 wt. % 1-lactide. The inherent viscosity of the copolymer was 0.50 dl/g (0.5 g/dl in CHCl$_3$).

EXAMPLE 4

Synthesis of ε-Caprolactone-1-Lactide Copolymer

ε-Caprolactone (30.0 g, 0.26 mole), 1-lactide (170.0 g, 1.18 mole), lauryl alcohol (5.10 g, 2.74×10$^{-2}$ mole) and stannous chloride dihydrate (0.0162 g, 7.2×10$^{-5}$ mole were combined in a stirred reactor under nitrogen at 180° C. The mixture was stirred at 180° C. for 3 hours. The resulting polymer had a composition, as determined by $^1$H NMR, of 3 wt. % ε-caprolactone and 87 wt. % 1-lactide. The ηinh was 0.27 dl/g (0.5 g/dl in CHCl$_3$).

EXAMPLE 5

Synthesis of ε-Caprolactone-Trimethylene Carbonate Copolymer

ε-Caprolactone (8.0 g, 0.070 mole), trimethylene carbonate (2.0 g, 0.020 mole), lauryl alcohol (0.283 g, 1.52×10$^{-3}$ mole) and stannous chloride dihydrate (2.02 mg, 8.91×10$^{-6}$ mole) were combined in a flask. The flask was flushed with nitrogen, evacuated and sealed. The flask was heated at 135° C. for 24 hours. The resulting polymer had a composition, as measured by $^1$H NMR, of 86 wt. % ε-caprolactone and 14 wt. % trimethylene carbonate. The ηinh of the copolymer was 0.26 dl/g (0.5 g/dl in HFAS).

EXAMPLE 6

Synthesis of ε-Caprolactone-Trimethylene Carbonate Copolymer

ε-Caprolactone (40 g, 0.35 mole), trimethylene carbonate (10 g. 0.098 mole), lauryl alcohol (1.42 g, 7.6×10$^{-3}$ mole) and stannous chloride dihydrate (10.1 mg, 4.5×10$^{-5}$ mole) were combined in a flask and heated for 24 hours under nitrogen at 135° C. The resulting polymer had an inherent viscosity of 0.42 dl/g (0.5 g/dl in HFAS). The composition was determined by $^1$H NMR to be 86 wt. % caprolactone and 14 wt. % trimethylene carbonate.

EXAMPLE 7

Synthesis of ε-Caprolactone-Glycolide Copolymer

ε-Caprolactone (170 g, 1.49 mole), glycolide (30 g, 0.26 mole), lauryl alcohol (1.37 g, 7.3×10$^{-3}$ mole) and stannous octoate (0.052 g, 1.2×10$^{-4}$ mole) were combined in a stirred reactor under nitrogen at 180° C. The mixture was stirred at 180° C. for 4.5 hours. The resulting polymer had an inherent viscosity of 0.68 dl/g (0.5 g/dl in CHCl$_3$). The composition was determined by $^1$H NMR to be 85 wt. % ε-caprilactone and 15 wt. % glycolide.

EXAMPLES 8-19

Synthesis of Caprolactone-Glycolide Copolymers

A series of random copolymers of ε-caprolactone and glycolide was prepared by the general procedure described in example 7. The bulk polymerizations were carried out in a stirred reactor under a slow nitrogen purge. The resulting polymers were dried in vacuum to remove residual monomer. Specific preparative details and properties of the resulting polymers are summarized in Table 1.

TABLE 1

Caprolactone/Glycolide Copolymers

| | Composition as Charged | | | | | | | | Analyzed Properties | | | |
|---|---|---|---|---|---|---|---|---|---|---|---|---|
| | ε-Caprolactone | | Glycolide | | Stannous Octoate | | Lauryl Alcohol | | Reaction Conditions | | NMR[3] | | inh[4] | DSC[5] |
| Example | grams | moles | grams | moles | mg. | moles (× 10$^{-5}$) | grams | moles (× 10$^{-3}$) | Hrs | °C. | Cap (wt %) | Gly (wt %) | CHCl$_3$ | Tm(°C.) |
| 8 | 170 | 1.49 | 30 | 0.26 | 28.0[1] | 12.4 | 4.10 | 220 | 3 | 175 | 84.1 | 15.9 | 0.34 | 42 |
| 9 | 170 | 1.49 | 30 | 0.26 | 18.5 | 4.57 | 0.163 | 0.875 | 4.5 | 180 | 85.2 | 14.8 | 0.82 | 48 |
| 10 | 127.5 | 1.12 | 22.5 | 0.194 | 38.7 | 9.56 | 0.113 | 0.606 | 5.75 | 180 | 84.7 | 15.3 | 1.10 | 38 |
| 11 | 127.5 | 1.12 | 22.5 | 0.194 | 38.7 | 9.56 | 0.122 | 0.655 | 5.0 | 175 | 84.3 | 15.7 | 1.39 | NC[2] |
| 12 | 95.0 | 0.832 | 5.0 | 0.0431 | 26.0 | 6.41 | 0.652 | 3.50 | 3.0 | 175 | 94.8 | 5.2 | 0.77 | 55 |
| 13 | 90.0 | 0.789 | 10.0 | 0.0862 | 25.8 | 6.38 | 0.652 | 3.50 | 3.0 | 175 | 89.4 | 10.6 | 0.73 | 48 |
| 14 | 87.5 | 0.767 | 12.5 | 0.108 | 26.0 | 6.41 | 0.652 | 3.50 | 3.0 | 175 | 86.8 | 13.2 | 0.70 | 46 |
| 15 | 85.0 | 0.745 | 15.0 | 0.129 | 26.0 | 6.41 | 0.652 | 3.50 | 3.0 | 165 | 84.3 | 15.7 | 0.70 | 41 |
| 16 | 80.0 | 0.701 | 20.0 | 0.172 | 25.9 | 6.40 | 0.650 | 3.49 | 3.0 | 177 | 79.1 | 20.9 | 0.72 | NC |
| 17 | 70.0 | 0.613 | 30.0 | 0.258 | 25.9 | 6.40 | 0.649 | 3.48 | 3.0 | 176 | 68.6 | 31.4 | 0.60 | NC |
| 18 | 50.0 | 0.438 | 50.0 | 0.431 | 25.7 | 6.35 | 0.647 | 3.47 | 3.0 | 176 | 47.0 | 53.0 | 0.48 | NC |
| 19 | 40.0 | 0.350 | 60.0 | 0.517 | 25.7 | 6.35 | 0.646 | 3.47 | 3.0 | 175 | 36.3 | 63.7 | 0.73 (HFAS) | NC |

[1]SnCl$_2$ 2H$_2$O was used as a catalyst in this sample.
[2]NC = Not crystalline at room temperature.
[3]NMR is Nuclear Magnetic Resonance Spectrometry.
[4]inh is inherent viscosity of a 0.5 g/dl solution of the polymer in the solvent. The solvents used were choloroform (CHCl$_3$) and hexafluoroacetone sesquihydrate (HFAS).
[5]DSC is Differential Scanning Calorimetry. Tm is the melting temperature (peak).

Table II summarizes the in vitro performance for the coatings of this invention.

TABLE 2

In Vitro Coating Performance

| Suture Coated with Example | Wt. % Cap in Copolymer | Wt. % Coating[1] | Knot Rundown[2] Wet | Snug-in Work[3] (kg mm) | Security Work[4] (kg mm) |
|---|---|---|---|---|---|
| Control | 0 | 0 | L | — | — |
| 1 | 100 | 1 | R/L | — | — |
| | | 2 | RC | — | — |
| | | 3 | RC | — | — |
| 2 | 100 | 1 | L | — | — |
| | | 2 | L | — | — |
| | | 3 | L | — | — |
| 3 | 84 | 0.2 | R | — | — |
| | | 0.3 | R | — | — |
| | | 0.5 | R | — | — |
| | | 0.6 | R | — | — |
| | | 1.0 | R | — | — |
| | | 1.2 | RW | — | — |
| | | 1.6 | RW | — | — |
| | | 2.4 | RW | — | — |
| 4 | 13 | 3 | L | — | — |

TABLE 2-continued

| | | | | | |
|---|---|---|---|---|---|
| 5 | 86 | 1 | RW | — | — |
| | | 2 | RW | — | — |
| | | 3 | RW | — | — |
| 6 | 86 | 1 | RW | — | — |
| | | 2 | RW | — | — |
| | | 3 | RW | — | — |
| 7 | 85 | 0.7 | RC | — | — |
| | | 1.1 | RW | — | — |
| | | 1.2 | RW | — | — |
| | | 1.7 | RW | — | — |
| 8 | 84.1 | 0.8 | RW | — | — |
| | | 1.5 | RW | — | — |
| | | 1.8 | RW | — | — |
| 9 | 85.2 | 0.2 | — | — | — |
| | | 0.9 | RC | — | — |
| | | 1.6 | RW | — | — |
| | | 2.2 | RW | — | — |
| 10 | 84.7 | 0.8 | — | — | — |
| | | 1.5 | — | — | — |
| | | 2.1 | — | — | — |
| 11 | 84.3 | 1.3 | RU | — | — |
| | | 2.1 | RD/L | — | — |
| | | 3.0 | RD | — | — |
| 12 | 94.8 | 0.72 | RC | 29.16 ± 3.18 | 22.08 ± 3.14 |
| | | 1.53 | RC | 26.24 ± 1.55 | 22.02 ± 0.54 |
| | | 2.11 | RC | 21.77 ± 2.78 | 23.82 ± 1.04 |
| 13 | 89.4 | 0.75 | R | 12.24 ± 8.53 | 20.85 ± 1.43 |
| | | 1.54 | R | 13.55 ± 11.00 | 22.28 ± 0.98 |
| | | 2.28 | RW | 20.33 ± 7.90 | 21.49 ± 1.11 |
| 14 | 86.8 | 0.76 | R | 4.66 ± 0.87 | 15.39 ± 1.76 |
| | | 1.49 | RW | 7.12 ± 1.65 | 17.89 ± 0.75 |
| | | 2.24 | RW | 8.46 ± 3.34 | 19.25 ± 0.75 |
| 15 | 84.3 | 0.76 | RW | 7.56 ± 3.75 | 12.46 ± 2.05 |
| | | 1.49 | RW | 4.37 ± 1.95 | 14.79 ± 1.74 |
| | | 2.22 | RW | 9.94 ± 4.10 | 14.50 ± 1.96 |
| 16 | 79.1 | 0.81 | RW | 1.82 ± 0.98 | 9.79 ± 1.75 |
| | | 1.59 | RW | 1.99 ± 0.59 | 11.16 ± 1.44 |
| | | 2.36 | RW | 2.03 ± 0.98 | 11.90 ± 1.90 |
| 17 | 68.6 | 0.73 | RW | 4.73 ± 3.21 | 13.83 ± 1.26 |
| | | 1.36 | R | 1.52 ± 0.49 | 14.12 ± 1.47 |
| | | 2.07 | R | 5.35 ± 3.62 | 14.61 ± 1.20 |
| 18 | 47.0 | 0.71 | RD/RC | 29.39 ± 1.81 | 20.09 ± 1.99 |
| | | 1.38 | RD/RC | 31.15 ± 0.88 | 20.61 ± 1.50 |
| | | 2.06 | RD/RC | 28.02 ± 1.58 | 18.84 ± 1.72 |
| 19 | 36.3 | 1.71 | RD | 44.39 ± 1.30 | 23.09 ± 0.45 |
| | | 3.07 | L/RU | 45.47 ± 2.90 | 23.67 ± 0.33 |
| | | 4.54 | L/RU | 39.20 ± 5.21 | 23.59 ± 0.49 |

TABLE 2 FOOTNOTES (1) The coatings were applied by hand dipping 1/0 polyglycolic acid braid in a 3% (wt./vol.) polymer solution in acetone for examples 1, 2, 4, 5, and 6. Coating levels for these examples were rounded to the nearest integer. Examples 3, 7, 8, 9, 10, and 11 were coated from a 2% (wt./vol.) solution in acetone using a capillary coating machine. the remainder of the samples were machine coated from a 3.5% (wt./vol.) solution in acetone or methylene chloride (example 19 only).
(2) Square knots were formed in the coated 1/0 polyglycolic acid braid using a conventional suture tying board. The knot was then run down to the board to assess the stick-slipping of the knot (chatter) as it runs down and to assess the force required to initiate and sustain the run-down. The abbreviations are: R, Runs; L, Locks; RC, Runs with Chatter; RD, Runs with Difficulty; RU, Runs with Unpredictability; RW, Runs Well. The comparisons are made on suture wet with saline.
(3) This test measures the ability of a suture (in this case 1/0 polyglycolic acid) to be snugged-in. A loop is passed around a steel rod and tied with a square knot. The knot is set to a prescribed tension with an Instron tester, and the tension is then removed. After resetting the gage length and removing the steel rod, the loop is tested to break. The force and crosshead movement are recorded by an attached computer which calculates the work needed to move the crosshead 15 mm. Samples were tested immediately after 30 seconds immersion in saline solution (0.9% NaCl in distilled water). The tensions used to set the knots, and all the other conditions of knot tying and testing, are practical laboratory conditions, but may not correspond to actual surgical practice. The knot snug-in may not correlate with clinical experience.
(4) A strand (in this case 1/0 polyglycolic acid) is tied to itself to form a loop using a square + 1 knot. The second and third throws of the knot are set to a prescribed tension, the loop is cut, and the cut ends are clamped in the jaws of an Instron tester. In the same way as was described above for snug-in, the work required to move the crosshead 10 mm is determined. Samples are tested immediately after 30 seconds immersion in saline solution.

Table 3 summarizes the in vivo performance for some of the bioabsorbable coatings of this invention.

TABLE 3

IN VIVO COATING EVALUATIONS[1]

| Coating Polymer From: | Wt. % Coating[2] | Knot Repositioning Ability[3] | Knot Security[4] | |
|---|---|---|---|---|
| | | | Category: 1 | 2 |
| Control | 0 | 0/8 | 4/4 | 0/4 |
| Example 3 | 0.6 | 7/18 | 14/14 | 0/14 |
| | 1.2 | 12/18 | 13/17 | 4/17 |
| | 1.8 | 10/18 | 16/18 | 2/18 |
| | 2.4 | 8/18 | 15/17 | 2/17 |
| Example 7 | 1.2 | 31/33 | 17/32 | 15/32 |
| | 1.8 | 27/27 | 20/27 | 7/27 |
| Example 9 | 1.7 | 24/24 | 15/24 | 9/24 |

[1]Coated, needled and sterilized sutures were tested in dogs.
[2]The coatings were applied to 1/0 polyglycolic acid braid from a 2% (wt./vol.) solution of the coating material dissolved in acetone.
[3]A suture coated with the test material is passed through two sides of a wound in the animal. A square knot is formed in the suture approximately 12-15 mm from the final knot position required to close the wound. The two ends of the suture are then pulled to slide the knot into position. Knots that slide properly are rated 1 while knots that fail to move into position are rated 0. The rating for a coating is the sum of the "1" ratings divided by the total number of test specimens.
[4]Immediate knot security is determined by using a pair of curved tweezers to tug at the 8 to 10 mm length of the ears of a square knot with two additional throws. Knots that are secure when manipulated are rated 1, knots with a loose top throw are rated 2, knots with an open top throw are rated 3, and knots that are not secure when manipulated are rated 4. The number of knots falling into each category is then divided by the total number of test specimens to provide a rating in each category. No values for categories 3 or 4 were reported for these examples.

We claim:

1. A surgical article having knot security and improved knot repositioning characteritics, the article comprising a strand, the strand having a bioabsorbable coating, the coating comprising a random copolymer, from about 50 to 85 percent by weight of the copolymer consisting of linkages of formula (I):

and the remaining linkages comprising at least one of the formulas (II) to (VIII):

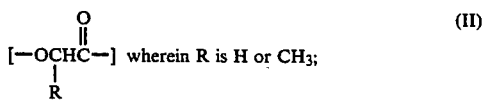
wherein R is H or CH$_3$;

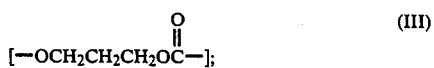

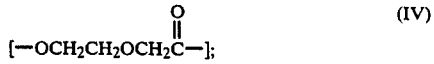

-continued

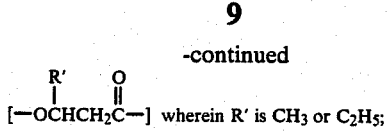  (V) [—OCHCH₂C—] wherein R' is CH₃ or C₂H₅;

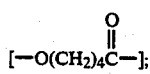  (VI) [—O(CH₂)₄C—];

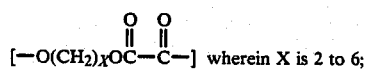  (VII) [—O(CH₂)ₓOC—C—] wherein X is 2 to 6;

and

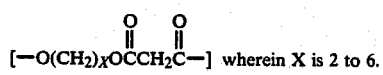  (VIII) [—O(CH₂)ₓOCCH₂C—] wherein X is 2 to 6.

2. An article of claim 1 wherein said remaining linkages are selected from the group consisting of formulas (II) and (III).

3. An article of claim 1 wherein said remaining linkages are selected from the group consisting of formula (II).

4. An article of claim 3 wherein the formula (II) is:

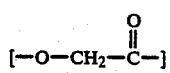
[—O—CH₂—C—]

5. An article of claim 3 wherein the formula (II) is:

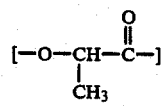
[—O—CH—C—]
        |
        CH₃

6. An article of claim 4 wherein said formula (I) is from about 65 percent by weight.

7. An article of claim 6 wherein said formula (I) is about 65 to 70 percent by weight.

8. An article of claim 6 wherein said formula (I) is about 85 percent by weight.

9. An article of claim 1 or 6 or 7 or 8 wherein the inherent viscosity of said copolymer is about 0.2 to 1.4 dl/g (0.5 g/dl in CHCl₃, 30° C.).

10. An article of claim 4 or 9 wherein the strand is bioabsorbable.

11. An article of claim 10 wherein the strand is manufactured from a polymer prepared from one or more monomers selected from the group consisting of lactides, carbonates and lactones.

12. An article of claim 10 wherein the strand is manufactured from a homopolymer prepared from the monomer glycolide.

13. An article of claim 10 wherein the strand is manufactured from a polymer prepared from at least the monomer lactide.

14. An article of claim 10 wherein the strand is manufactured from a copolymer prepared from the monomers glycolide and 1,3-dioxan-2-one.

15. An article of claim 13 wherein the strand is manufactured from a copolymer prepared from the monomers glycolide and lactide.

16. An article of claim 10 wherein the strand is in multifilamentary form.

17. An article of claim 16 wherein said coating comprises about 1/10 to 5 percent by weight of the coated strand.

18. An article of claim 17 wherein said coating comprises about ½ to 3 percent by weight.

19. A surgical suture or ligature comprising a bioabsorbable, multifilamentary strand manufactured from a polymer prepared from one or more monomers selected from the group consisting of glycolide, lactide, 1,3-dioxan-2-one and 1,4-dioxan-2-one, the strand having a bioabsorbable coating, the coating comprising a random copolymer, from about 65 to 85 percent by weight of the coating copolymer consisting of linkages of formula (I):

[—O(CH₂)₅C—]  (I)

and the remaining linkages comprising at least the formula (II):

[—OCH₂C—],  (II)

wherein the inherent viscosity of said copolymer is about 0.2 to 1.4 dl/g (0.5 g/dl in CHCl₃, 30° C.), and said coating comprises about 1/10 to 5 percent by weight of the coated suture or ligature.

20. An article of claim 19 wherein said formula (I) is about 70 percent by weight of the coating copolymer.

21. An article of claim 19 wherein said formula (I) is about 85 percent by weight of the coating copolymer.

22. An article of claim 19 wherein the strand is manufactured from a homopolymer prepared from the monomer glycolide.

23. An article of claim 19 wherein the strand is manufactured from a polymer prepared from at least the monomer lactide.

24. An article of claim 19 wherein the strand is manufactured from a copolymer prepared from the monomers glycolide and 1,3-dioxan-2-one.

25. An article of claim 23 wherein the strand is manufactured from a copolymer prepared from the monomers glycolide and lactide.

26. An article of claim 19 wherein said coating comprises about ½ to 3 percent by weight of the coated suture or ligature.

* * * * *